United States Patent [19]

Eichner et al.

[11] Patent Number: 5,994,311
[45] Date of Patent: Nov. 30, 1999

[54] CELL ADHESION PEPTIDES FOR MODIFYING THE ADHESION CAPACITY OF EUKARYOTIC CELLS BETWEEN EACH OTHER

[75] Inventors: Wolfram Eichner, Butzbach; Katharina Kock, Friedberg; Heiko Mielke, Neu Wulmstorf; Albrecht Doerschner, Hamburg, all of Germany

[73] Assignee: Beiersdorf AG, Hamburg, Germany

[21] Appl. No.: 08/793,264

[22] PCT Filed: Aug. 8, 1995

[86] PCT No.: PCT/EP95/03135

§ 371 Date: May 2, 1997

§ 102(e) Date: May 2, 1997

[87] PCT Pub. No.: WO96/06114

PCT Pub. Date: Feb. 29, 1996

[30] Foreign Application Priority Data

Aug. 22, 1994 [DE] Germany ............... 44 30 601

[51] Int. Cl.⁶ .................. A61K 38/06; A61K 38/08; A61K 38/16; A61K 38/39
[52] U.S. Cl. .................. 514/18; 530/324; 530/325; 530/326; 530/327; 530/328; 530/329; 530/330; 530/331; 530/350; 530/356; 530/363; 530/385; 530/403; 514/12; 514/13; 514/14; 514/15; 514/16; 514/17; 435/7.21; 435/371; 435/372
[58] Field of Search .................. 530/327, 324, 530/331, 325, 350, 326, 356, 328, 363, 329, 385, 330, 403; 514/13, 12, 14, 15, 16, 18, 17; 435/7.21, 371, 372

[56] References Cited

U.S. PATENT DOCUMENTS 5,026,636 6/1991 Baseman et al. .
5,225,193 7/1993 Bartfai .............................. 424/88
5,298,420 3/1994 Chang .............................. 435/240.27
5,532,305 7/1996 Matsuzaki .............................. 525/54.2

FOREIGN PATENT DOCUMENTS

WO-A-91 18294 11/1991 WIPO .
WO-A-92 06199 4/1992 WIPO .
WO-A-92 13887 8/1992 WIPO .

OTHER PUBLICATIONS

Rozdzinski, E, et al., Antiinflammatory effects in experimental meningitis of prokaryotic peptides that mimic selectins. J. Infect. Dis. 168:1422–1428, 1993.
Rozdzinski, E., et al., Prokaryotic peptides that block leukocyte adherence to selectins. J. Exp. Med. 178:917–924, Sep. 1993.
Gross, E, et al. In Peptides, Apr. 1974, Wolman, Y, ed. John Wiley & Sons, New York and Israel Universities Press, Jerusalem, pp. 403–413.
Edgington, S.M. Biotechnology. 10:383–389, 1992.
Tabor's Cyclopedic Medical Dictionary, pp. 725–726, 1981.
Dallo et al., J. Exp. Med. (1988) 167(2), 718–23 Coden: JEMEAV, ISSN: 0022–1007 Identification of P1 gene domain containing epitope(s) mediating Mycoplasmy pneumoniae cytadherene.
Biochemicalien—Organische Verbindingen voor Research en Diagnostics catalogus by Sigma Chemie, 1994 Benelux edition, pp. 1076–1078.

*Primary Examiner*—David Saunders
*Assistant Examiner*—Mary Beth Tung
*Attorney, Agent, or Firm*—Nixon & Vanderhye P.C.

[57] ABSTRACT

The invention relates to adhesion peptides for modifying the adhesion capacity of eukaryotic cells between each other and their use to promote or inhibit the cell/cell adhesion of eukaryotic cells. The invention relates in particular to the use of the cell adhesion polypeptides in the manufacture of pharmaceuticals to influence the cell/cell interactions of eukaryotic cells.

26 Claims, 3 Drawing Sheets

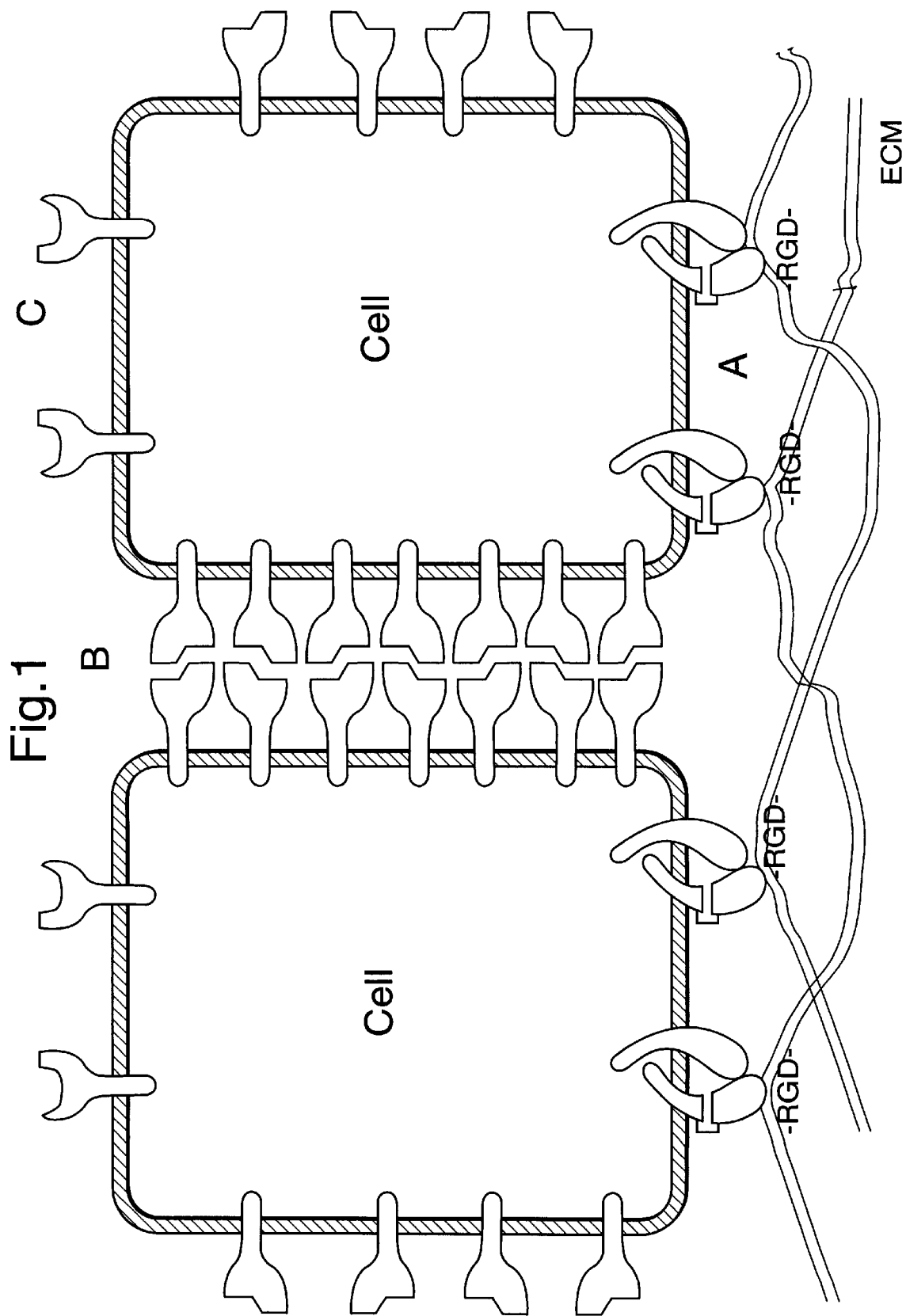

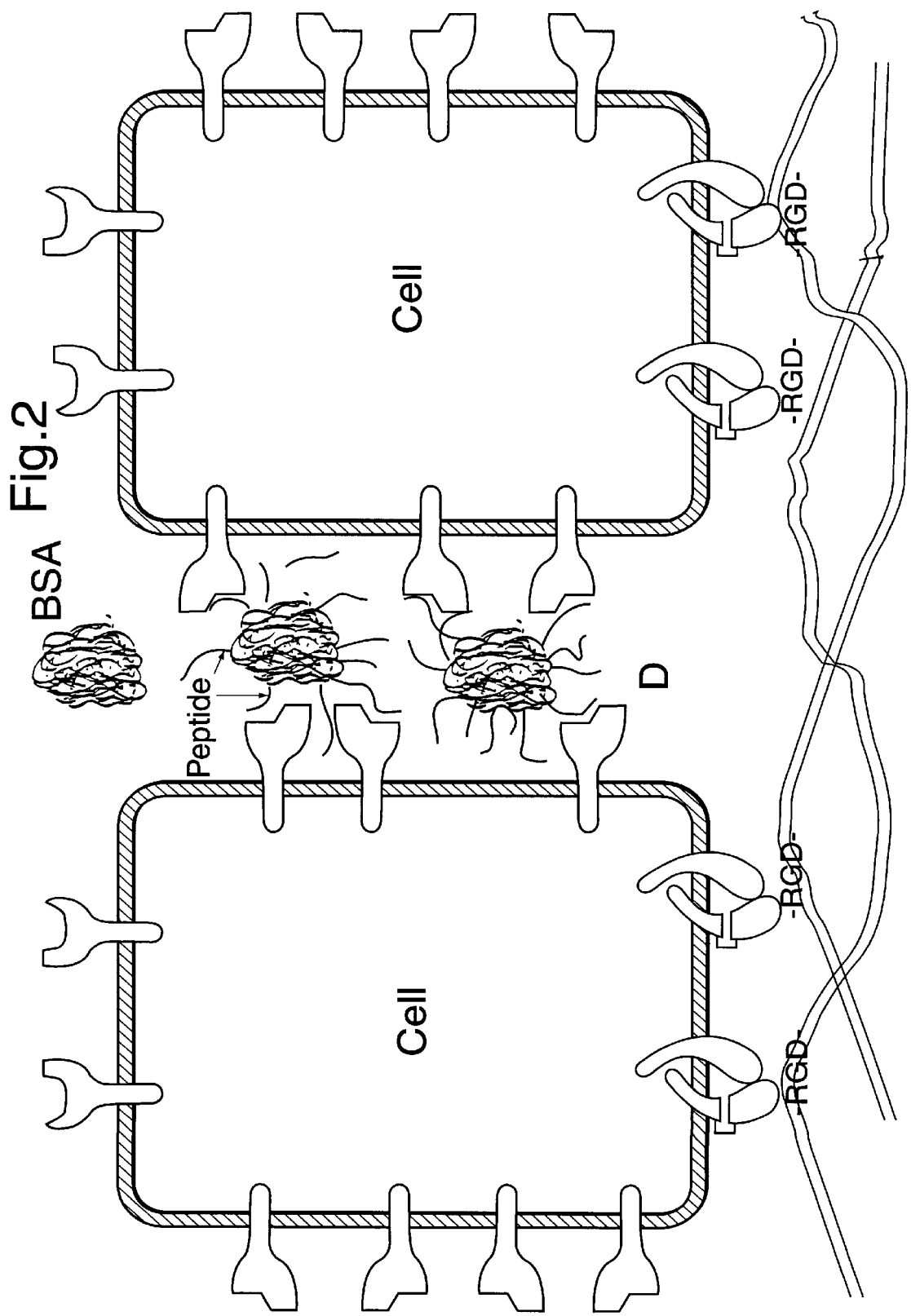

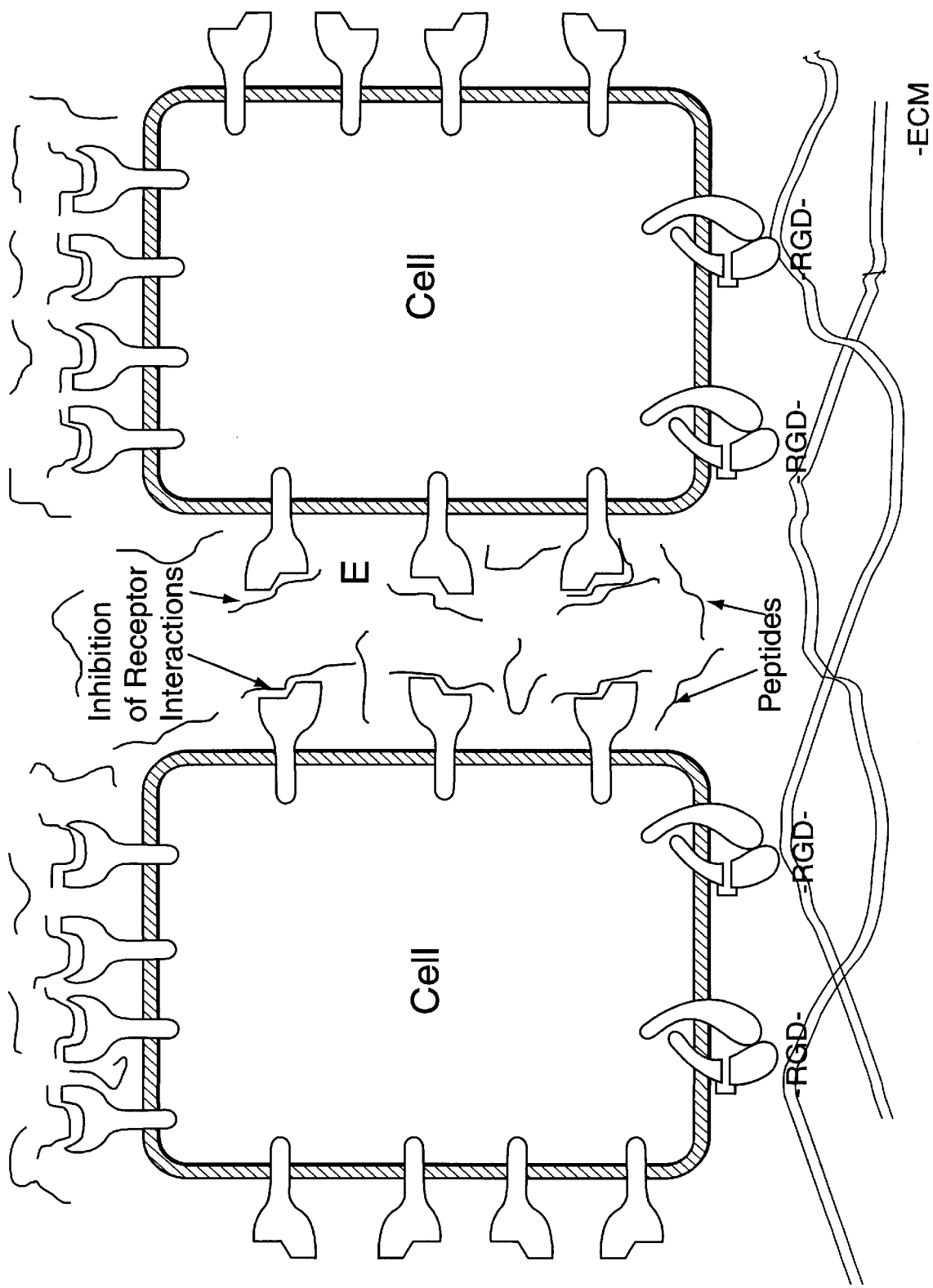

CELL ADHESION PEPTIDES FOR MODIFYING THE ADHESION CAPACITY OF EUKARYOTIC CELLS BETWEEN EACH OTHER

This application is a 371 of PCT/EP95/03135, filed Aug. 8, 1995.

The present invention relates to adhesion peptides for modifying the adhesion capacity of eukaryotic cells between each other and their use to promote or inhibit the cell/cell adhesion of eukaryotic cells. The invention relates in particular to the use of the cell adhesion polypeptides in the manufacture of pharmaceuticals to influence the cell/cell interactions of eukaryotic cells.

The term "(cell) adhesion"/"cell adhesiveness" is used in the narrower sense to describe the way in which cells adhere to another, e.g. as a result of the binding of complementary membrane surface molecules. The term "adherence" is commonly used in the art of cell culturing for cells which bind in vitro to solid surfaces. The terms "(cell) adhesion" and "adherence" are often used synonymously.

The cells of the various tissues or organs of a multi-celled organism possess a specific function in a defined environment. Apart from a small number of exceptions, such as the cells circulating in the vascular system for example, eukaryotic cells are as a rule fixed firmly in place. This immobilisation is mediated by two kinds of adhesion, namely cell/cell interactions on the one hand, and cell/matrix interactions on the other. The intercellular contacts, i.e. cell/cell interactions (FIG. 1B) are supported in particular at the cellular basal membrane by a heterogeneous network of fibres, rather like scaffolding, which is referred to as the extracellular matrix (ECM), consisting of proteins, glycoproteins (for example: fibronectins, the collagens, laminin, thrombospondin and vitronectin) and other macromolecules associated with the basal membrane (for example: proteoglycanes and glucosaminoglucanes), i.e. by forming cell/matrix interactions (FIG. 1A). A reorganisation of these adhesion structures occurs for example in the course of repair processes, such as the healing of wounds, or in the formation and growth of tumours.

The two kinds of adhesion, i.e. the cell/cell and the cell/matrix interactions, are shown schematically in FIGS. 1A and 1B. From that illustration, it can be seen that the interaction between cells and the extra-cellular matrix is promoted by different types of structures, similar to the "lock and key principle". Cell/cell adhesion, on the other hand, mainly takes place through interaction between similar types of cell surface structures, i.e. by similar molecules with a receptor character.

Among the ECM factors which promote cell/matrix adhesion on the parts of the basal membrane, a particular role is played by fibronectins. In its native form, the fibronectin molecule is a dimer composed of identical sub-units with a relative molecular mass $M_r$ of 220 KD in each case, which are linked together via disulphide bridges. One feature that is particularly pronounced in fibronectin, as also on other proteinogenic ECM components, is its composition of short repeating amino acid sequence units. Several of these sequences, which are homologous—though not identical—to one another, for their part form clearly delimited domains in the individual fibronectin chains, and these domains facilitate binding to fibrin, collagen or heparin. Only one of these domains possesses the ability to bind to cells. The section of the sequence responsible for the ability of this fibronectin domain to adhere to cells was identified and sequenced by Pierschbacher et al. (Proc. Natl. Acad. Sci. USA 80 (1983) 1224–1227). This section contains the tetrapeptide "RGDS" (Arg-Gly-Asp-Ser). This recognition sequence was characterised by Pierschbacher and Ruoslahti (Nature 309 (1984) 30–33), by testing smaller and smaller synthetic peptides of the cell recognition domains with regard to their ability to promote cells' adhesion capacity. The RGD sequence (Arg-Gly-Asp) is essential in promoting the binding activity, whereas the amino acid serine in position 4 can also be replaced by other amino acids (Pierschbacher and Ruoslahti, loc. cit.).

The RGDX sequence has been found not only in the fibronectin molecule, but also in numerous other matrix proteins, the X standing for a variable, though not optional, amino acid (cf. Humphries, J. Cell Sci. 97 (1990) 585–592).

By now, it is known that recognition of the RGDX sequence is ensured by receptors on the target cells, and that it takes the form of highly specific interactions between receptors on the cell surface and the matrix. The receptor molecules, referred to as integrins, are heterodimers constructed of and sub-units (FIG. 1A). On the part of the ligands which interact with the integrins, the specificity of the RGDX sequence effecting adherence is caused by the immediately adjacent sequence sections (Pierschbacher and Ruoslahti, J. Biol. Chem. 262 (1987), 17294–17298). The consequence of this is that, despite having an identical RGD core sequence, ECM components interact with integrin heterodimers of widely varying compositions, i.e. with special receptors (for a review, see, for example, Dedhar, Bio Essays, 12 (1990), 583–590 and Hynes, Cell 69 (1992), 11–25).

The highly conserved amino acid sequence of the "RGD" tripeptide has been detected not only in proteins of the extracellular matrix, but also in various bacterial and viral proteins, and their adherence mediating function in those proteins has been demonstrated experimentally. Thus pertactin, a surface protein from *Bordetella pertussis* (Leininger et al., Proc. Natl. Acad. Sci. USA 88 (1991) 345–349), and also the "tat" (type 1 transactivation protein) of the human HIV-1 virus (Brake et al., J. Cell Biol. 111 (1990) 1275–1281), and then also an adenovirus surface protein (Nemerow et al., Trends in Cell Biol. 4 (1994) 52–55), contain the RGD sequence motif.

One thing which the adhesion proteins known in the prior art and the peptide sequences identified thereupon have in common is that they facilitate the interactions between the cell and the matrix, or promote cell/matrix adhesion. Apart from the interaction with the extra-cellular matrix, cells likewise interact with one another, this cell/cell adhesion being effected by specific surface receptors on both sides. This means that, unlike the cell/matrix interaction, in which the ECM component(s) and cell surface receptor(s) begin to interact with one another according to the "lock and key principle", it is as a rule similar molecules (i.e. molecules with a receptor character) which are involved in the interaction in the case of cell/cell adhesion.

An investigation into "adhesion factors", as they are known, is of great interest, since their central role in all processes of cell/cell interaction or cell migration is becoming more and more apparent (Travis, Science 260, (1993), 906–908). In the development of an embryo, adhesion molecules are needed for tissues and organs to form. Apart from that, these factors are involved to a decisive extent in wound repair processes, for example, inflammatory processes and the metastasis of cancer cells.

It is therefore an object of the present invention to provide novel adhesion peptides which effectively influence the intercellular interactions of eukaryotic cells, i.e. adhesion peptides which modify the adhesion capacity of eukaryotic cells between each other, such as endothelial cells, for example, or human epidermal cells. It is intended that such peptides should be obtainable in a simple manner and be suitable for use both in promoting and in inhibiting the cell/cell adhesion of eukaryotic cells. In particular, it is intended to be possible for the peptides to be used not only for the in vitro modification of the adhesion capacity of eukaryotic cells between each other, such as for the preparation of skin grafts and the production of artificial blood vessels, for example, and also in the manufacture of pharmaceuticals to influence the cell/cell adhesion of eukaryotic cells, for example to increase the rate at which skin grafts or organ transplants grow on, and that it should also be possible to use them for the other applications mentioned above.

The peptides of the present invention are capable of effectively influencing intercellular adhesion processes, i.e. cell/cell interactions, and are thus extremely useful aids which are suitable for a wide range of applications. In an immobilised form, for example by being coupled to carrier molecules, they can be used as a substrate for a wide range of cell types, for example to promote cell attachment processes or wound repair processes in general. They can be used as a component of resorbable wound dressings effectively to accelerate the colonialisation of wounds, such as burns, by promoting cell migration, and also as an adherence substrate for endothelial cells lining blood vessels etc. in the development of replacement vessels. The mechanism by which adhesion peptides work when coupled to a substrate in order to mediate cell/cell contacts is shown schematically in FIG. 2D.

Galenical preparations of peptides effective in adhesion can serve in a particularly preferred embodiment also to improve the growing rate of skin grafts. So far, in about 40% of transplantations, and in as many as 60% of skin transplantations in the case of burns, graft failure occurs, in which the graft does not grow on. The use of peptides effective in intercellular adhesion can effectively promote the interactions between the graft and the bed of the wound, thus substantially increasing the likelihood that the transplantation will be successful. In addition, it is also possible to use them in preparing skin grafts. Furthermore, conjugates of adhesion effective peptides and pharmaceutical active agents can be manufactured, as a result of which it can be ensured that the active agents can be brought in a more targeted manner to receptors on the target cell because of the highly specific binding affinity of the peptide portion.

In a soluble form, it is also possible to achieve contrary effects, i.e. the inhibition of cell adhesion, using factors of this kind, since a competitive inhibitory effect occurs when surface receptors are specifically saturated (shown schematically in FIG. 3E). In a number of pathological processes, such as arteriosclerotic or thrombotic lesions, there is an excessive stimulation of adhesion processes on the vessel surface, leading to a narrowing of the vessels, which can even reach the stage of occlusion of the vessel concerned. The adhesion inhibiting peptides of the present invention can counteract such a pathological process in a specific manner. Inhibition of cell adhesion is particularly desirable in order to attenuate inflammatory processes, it being possible in this way specifically to influence the receptor-mediated entry of inflammation cells from the vascular system into the tissue. Other possible uses of peptides effective in adhesion inhibition are the prophylaxis of arteriosclerosis and thrombosis. In addition, adhesion peptides can be utilised in cosmetic/dermatological preparations, such as remedies for the prevention of widespread dandruff or cutaneous scale.

The adhesion peptides of the present invention which modify the adhesion capacity of eukaryotic cells between each other, i.e. which either increase or inhibit the intercellular adhesion of eukaryotic cells, are characterised by having at least the amino acid sequence
Aa3-Aa2-Aa1-(AaX)$_n$-(AaY)$_m$ (SEQ ID NO: 33),
wherein
n is either 0 or 1,
m is either 0 or 1 when n=1, and
Aa1 indicates the terminal amino acid at the carboxy terminal end of the peptide when n=m=0, and wherein
AaX and AaY are any optional amino acid in each case,
Aa1 is Gly, Pro or Asp,
Aa2 is Asp, Leu, Asn or Ser, and
Aa3 is Leu, Ile, Phe or Gly.
(In the above-mentioned formula, m is 0 if n is 0.)

The amino acids are designated in accordance with their three-letter code (or one-letter code). The meaning of the abbreviations is as follows: Ala (or A)=alanine, Arg (or R)=arginine, Asn (or N)=asparagine, Asp (or D)=aspartic acid, Cys (or C)=cysteine, Gln (or Q)=glutamine, Glu (or E)=glutamic acid, Gly (or G)=glycine, His (or H)=histidine, Ile (or I)=isoleucine, Leu (or L)=leucine, Lys (or K)=lysine, Met (or M)=methionine, Phe (or F)=phenylalanine, Pro (or P)=proline, Ser (or S)=serine, Thr (or T)=threonine, Trp (or W)=tryptophan, Tyr (or Y)=tyrosine, and Val (or V)=valine.

In the context of the present invention, the above-mentioned amino acids can also be replaced by modified amino acids, such as hydroxylysine (Hy1) instead of lysine. Correspondingly modified or rare amino acids which can be used in accordance with the invention are listed in WIPO Standard ST. 23 (Official Journal of the European Patent Office 12/1992, pp. 9 ff., item 12). In the case of amino acids which occur as optical isomers, both the D and the L forms can be used, the L isomers being preferred in accordance with the invention.

The term "adhesion peptide" or "peptide" is used in the context of the present invention for amino acid sequences in general with at least three amino acids linked together via the ordinary peptide bonds (amide bonds). The chain length of these amino acid chains can vary, with preference being given to peptides (or oligopeptides or polypeptides) extended at the amino terminus (i.e. at Aa3) having up to 30, preferably 20, amino acids. The adhesion peptides of the invention are preferably present in linear form, though branched amino acid chains are also conceivable without there being any inevitable reduction in the influencing effect on cell/cell adhesion as a result.

In accordance with one preferred embodiment of the invention, peptides are provided which possess at least the amino acid sequence
Aa4-Aa3-Aa2-Aa1-(AaX)$_n$-(AaY)$_m$ (SEQ ID NO: 34),
where
n, m, AaX, AaY, Aa1, Aa2 and Aa3 have the same meaning as that specified above, and Aa4 is Leu or Ser.

Especially preferred are peptides which possess at least the amino acid sequence
Aa5-Aa4-Aa3-Aa2-Aa1-(AaX)$_n$-(AaY)$_m$ (SEQ ID NO: 35),
where
n, m, AaX, AaY, Aa1, Aa2, Aa3 and Aa4 have the same meaning as that specified above, and Aa5 is Glu, Ser, Asp or Asn.

In the adhesion peptides of the invention with n=1 and m=0 or n=m=1, glutamic acid (Glu) and/or glycine (Gly) are preferably used as the amino acid(s) AaX or AaY. According to a particular embodiment of the present invention, the amino acids AaX and AaY are completely absent, Aa1 forming the terminal amino acid at the carboxy terminal end of the peptide.

The adhesion peptides of the present invention are characterised by characteristic sequence features both in the region of the carboxy terminus and in the amino terminal region. It has been established that, among the peptides listed above and defined by the general formulae, those adhesion peptides are especially advantageous which have 6 to 30 amino acids, preferably 12 to 14 amino acids, and whose amino acid at the amino terminal end of the peptide is Gly, Ser, Leu, Ile, Arg or Thr. The adhesion capacity between eukaryotic cells can be modified particularly effectively if the amino terminal amino acid is Gly.

The amino acids in positions 3 and 5 from the carboxy terminal end (Aa3 or Aa5) are likewise especially important in influencing the cell/cell adhesion of eukaryotic cells, and it is advantageous to use the amino acids Leu (as Aa3) and/or Glu (as Aa5). In the case of peptides with a length of at least 5 amino acids, the simultaneous use of Leu and Glu in positions 3 and 5 is most preferred.

In addition, it has been established that the tripeptide Leu-Asp-Gly (AP#27) is already capable of effectively influencing the adhesion capacity of eukaryotic cells between each other. This amino acid sequence can also be found in the pentapeptide Glu-Leu-Leu-Asp-Gly (AP#25) and in the heptapeptide Leu-Ala-Glu-Leu-Leu-Asp-Gly (AP#21), which can influence the intercellular adhesion of eukaryotic cells just as effectively as the above-mentioned tripeptide Leu-Asp-Gly. The pentapeptide which has the amino acids Leu and Glu in positions 4 and 5 (Aa4 and Aa5) (AP#25) is even somewhat more effective than the tripeptide in modifying the adhesion capacity of eukaryotic cells between each other, which is evidence of the advantageous influence of the last-mentioned amino acids in peptides with a length of at least five amino acids.

The peptides
Leu-Ala-Glu-Leu-Leu-Asp-Gly-Glu-Gly (AP#19) and
Leu-Ala-Glu-Leu-Leu-Asp-Gly-Glu-Gly-Glu (AP#20),
which comprise the sequence of the heptapeptide AP#21 extended by one or two amino acids at the carboxy terminus, exhibit an increased adherence promoting effect compared to AP#21.

The sequence
Gly-Ile-Val-Arg-Thr-Pro-Leu-Ala-Glu-Leu-Leu-Asp-Gly (AP#6)
has proven particularly effective as adhesion peptides with 12 to 14 amino acids used in the context of the present invention. The deletion of the amino acid Leu in position 7 from the carboxy terminal end of the last-mentioned oligopeptide leads to the particularly effective dodecapeptide
Gly-Ile-Val-Arg-Thr-Pro-Ala-Glu-Leu-Leu-Asp-Gly (AP#7),
which exhibits a particularly successful effect in influencing the intercellular adhesion of eukaryotic cells. The two adhesion peptides are characterised both by the amino terminal amino acid Gly and by the amino acid sequence Glu-Leu-Leu-Asp-Gly (cf. SEQ ID NO: 25).

Studies of the peptides AP#7, AP#14, AP#16 and AP#24, which do not have leucine (Leu) in amino acid position 7 (Aa7), show that this amino acid does not have any positive, i.e. adherence promoting, influence in the sequence position concerned. The amino terminal sequence preferred in accordance with the invention is therefore
Gly-Ile-Val-Arg-Thr-Pro (cf. SEQ ID NO: 32).

Other adhesion peptides with 12 and 18 amino acids which are very effective at modifying the adhesion capacity of eukaryotic cells between each other are
Gly-Gly-Gly-Ser-Gly-Gly-Gly-Ser-Ser-Gly-Ser-Gly (AP#10),
Gly-Gly-Gly-Ala-Gly-Gly-Gly-Ser-Ser-Gly-Ser-Gly (AP#11) and
Gln-Ile-Asp-Phe-Asn-Arg-Leu-Phe-Thr-His-Pro-Val-Thr-Asp-Leu-Phe-Asp-Pro (AP#1).

The adhesion peptides made available in the context of the present invention can be manufactured synthetically in a simple manner, preferably by automation, i.e. using a commercially available peptide synthesiser. In addition, for smaller fragments, it is conceivable to have recourse to natural oligopeptides or polypeptides, though preference is to be given to the automated manufacture of the adhesion peptides because of the simplicity, precision and degree of purity of this method of synthesis.

The adhesion peptides of the invention are suitable both for promoting and for inhibiting or reducing the cell/cell adhesion of eukaryotic cells. If, for example, cells are contacted with the above-mentioned peptides, there is a competitive reaction with the natural receptor-like surface structures of the eukaryotic cells, which leads to a reduction of the adhesion capacity, i.e. to an inhibition of cell/cell adhesion.

According to one specific embodiment of the invention, the adhesion peptides can also be bound to carriers. A precondition for the selection of a suitable carrier molecule is that the functional biological activity of the peptide(s) should not be impaired either by the carrier or by the coupling process. Carrier molecules for the purposes of the invention can belong to very varied classes of substances.

From the class of substances comprising carbohydrates/polysaccharides, it would, for example, be possible to use glycanes, such as starch, glycogen, cellulose, pectin, amylose, dextran, polysucrose or chitosan. Similarly, it is possible to use glucosaminoglycanes, such as heparin, chitin, chondroitin sulphate, hyaluronic acid or lipopolysaccharides.

Some selected examples of the class of substances comprising proteins/polypeptides are components of ECM, such as collagen, immunoglobulins, BSA, KLH (keyhole limpet haemocyanin), ovalbumin, polylysine or lipoproteins. In addition, it is possible to conjugate the peptides of the invention to synthetic polymers, e.g. polyethylene glycol (PEG) or polyvinyl alcohol, to (phospho)lipids, such as ceramides or paraffin, for example, and to alcohols, e.g. glycerol.

The chemical coupling is as a rule effected directly via reactive groups of the carrier and the peptide or with the aid of "linkers" (linking molecules). In accordance with the invention, the bi-functional linker sulphosuccinimidyl-4-(N-maleimidomethyl)-cyclohexane-1-carboxylate (sulpho-SMCC) was used to couple the peptides to BSA. The groups capable of coupling can be present on the carrier and the peptide, but they can also be introduced by activating a reactive group in the molecule. Common reactive functions are, for example, the amino ($NH_2$), imino (imidazol ring), hydroxyl (OH), sulphohydryl (SH) or carboxyl (COOH) groups.

An advantageous method used in accordance with the invention is to couple peptides provided with a carboxy terminal cysteine to the carrier molecule (BSA), after that has previously been activated with the sulpho-SMCC linker.

If it is intended that the peptide/carrier conjugate should possess adhesion promoting properties, at least two peptide molecules must be bound to a single carrier. Carrier molecules to which only a single peptide is bound as a consequence of the coupling action possess binding properties similar to those of free peptides, i.e. peptides not bound to a carrier. Similar to the situation with free peptides described in FIG. 3E, they have the effect of inhibiting adhesion by saturating epitopes on the receptor molecules. Finally, the cells modified in this way are no longer capable—or or are only capable to a considerably reduced extent—of adhering to neighbouring eukaryotic cells.

If there are at least two adhesion peptides bound to a single carrier unit, on the other hand, the adhesion capacity of eukaryotic cells between each other is promoted, since in each case a carrier-coupled peptide adheres to a cell and another peptide on the same carrier facilitates adhesion to a neighbouring cell. In practice, depending on the nature of the carrier used, it is preferable that substantially more than two peptides should be bound to a single carrier unit (about 20 in the case of BSA), in order to promote cell/cell adhesion effectively.

The adhesion peptides of the present invention are suitable for promoting or inhibiting the mutual intercellular inter actions among any eukaryotic cells, i.e. there is virtually no restriction with regard to the eukaryotic target cells. It is thus just as possible, for example, effectively to modify the capacity of dermal and epidermal cells to adhere to their respective neighbouring cells as it is to modify the capacity of endothelial cells, differentiated cells of certain organs (such as liver cells, kidney cells, etc.) or cancer cells to adhere to one another in each case or to other eukaryotic cells.

In consequence, the adhesion peptides of the invention can be used for a wide variety of in vitro and in vivo applications in which the attachment or adhesion capacity of eukaryotic cells between each other plays a role. In this connection, reference can be made to the fields of application mentioned above with regard to the object of the present invention, for which the adhesion peptides of the invention are advantageously suitable.

In particular, the peptides of the present invention are suitable, for example, in the production of artificial blood vessels, promoting the mutual adhesion of the endothelial cells lining the blood vessels. The increase in the adhesion capacity of epidermal cells which is achieved when the adhesion peptides are used can be utilised above all in the preparation of skin grafts, where suitable culture vessels which are already used for this purpose in the prior art are coated with the peptides in order to promote the formation of an even artificial skin graft. For the applications in which the peptides of the invention are intended to exert a positive influence on the adhesion capacity, i.e. in those cases in which it is intended to promote the cell/cell interaction, the adhesion peptides are present in a form bound to carriers, with at least two peptides bound to one carrier unit in each case. In a particularly preferred embodiment, and depending on the nature of the carrier used, far more peptides can be bound to one and the same carrier.

In cases in which adhesion between eukaryotic cells is undesirable, i.e. in cases in which isolated cells or suspensions of single cells are needed in preference, the adhesion peptides of the invention can likewise be used successfully. Here, in order to saturate the surface structures of the cells which affect adhesion, either the isolated peptides are used or peptide/carrier conjugates are employed in which only one peptide is bound to one carrier unit in each case.

Wound repair processes in the skin occur in the form of two processes which can be distinguished from one another: contraction and epithelialisation. The latter process relates only to the epithelial cell layers. About 24 hours after the lesion occurs, migration of the keratinocytes begins, which continues until the lesion is occluded (Peacock, 1984, Wound Repair 3rd ed., W. B. Saunders Co., Philadelphia).

Substances which act as chemotactic attractors for epidermal cells can accelerate the epithelialisation of wounds and thus wound repair processes in the skin. It is conceivable to use the peptides of the invention as chemotactic attractors, because it has been possible to demonstrate the chemotactic effect for some peptides serving as examples.

The in vivo application of the adhesion peptides of the invention is just as varied as their use in vitro, because it is possible to use the peptides to intervene more or less anywhere in the human or animal organism where adhesion processes between eukaryotic cells play a role. It is, for example, possible to use the adhesion peptides to increase the speed at which skin grafts or organ transplants (such as in the liver or kidney) grow on, and it is also possible effectively to promote wound repair by influencing the cell/cell interactions. The inhibition of cell/cell adhesion, on the other hand, plays an important role, for example in the prophylaxis of thrombosis and/or arteriosclerosis, and also in suppressing the metastasis of cancer cells, in other words in cases in which the adhesion of eukaryotic cells between each other is undesirable, because they lead to pathological or subsequently even to fatal changes in the organism. With the aid of the adhesion peptides of the present invention, it is possible effectively to reduce or completely to suppress the formation of such accumulations of cells.

For in vivo application, the adhesion peptides are preferably present in the form of galenical preparations, i.e. in the form of pharmaceuticals which contain not only the peptides of the invention, but also carrier materials, adjuvants and/or additives, with the peptides either not linked to the abovementioned carriers or—depending on whether the pharmaceutical is intended to inhibit or promote the adhesion capacity of eukaryotic cells between each other—with one or at least two peptides bound to a carrier unit.

In the event that the pharmaceutical composition is intended to promote cell/cell adhesion, the adhesion peptides bound to one carrier unit in each case can, in each case, be identical to or different from one another.

In addition, the peptides of the invention are also suitable for the qualitative and/or quantitative determination of the cell/cell adhesion of eukaryotic cells (in vitro and in vivo).

The present invention will now be described with reference to examples.

EXAMPLES

All the peptide sequences investigated here and modified variants of these sequence patterns derived therefrom, and also all the control peptides where manufactured by peptide synthesis. As positive controls, synthetic peptides produced from ECM molecules which had an effect on adhesion were used. Both the fibronectin (FN) fragments IVA1 and IVA1b (designation by analogy with W084/00540) which were tested for comparative purposes contain the sequence pattern arginine-glycine-aspartic acid (Arg-Gly-Asp or RGD) (Pierschbacher and Ruoslahti, Nature 309 (1984) 30–33) and make it possible to demonstrate that the peptides of the invention, unlike the "RGD peptides" which influence the cell/matrix interaction, effectively influence the interactions of eukaryotic cells. Similarly, the amino acid sequence SVTLG was tested. The sequence SVTXG (X=variable amino acid) is found in human thrombospondin, which plays a major role in the aggregation of thrombocytes (cf. Prater et al., J. Cell Biol. (1991) 1031–1040). A further positive control used was an adhesion promoting fragment, referred to as P-15, of the α-1(I) chain of collagen (WO 91/02537).

It is known in the prior art that different physical properties of peptides can have an influence on the capacity of those peptides to adhere to the surface of a culture vessel. For this reason, the additional amino acid "cysteine" was attached at the carboxy terminus to all the tested peptides of the invention. The SH function of cysteine was needed in order to couple the peptide to corresponding carrier molecules. By means of an appropriate conjugation of the peptides to carrier substances, biophysical differences are largely compensated for.

1. Peptide Synthesis and Characterisation

All the peptides tested were synthesised in accordance with the solid phase synthesis method of Merrifield (R. B. Merrifield J. Am. Chem. Soc. 85 (1963) 2149–2154; cf. also Fields & Noble, Int. J. Protein Res. 35 (1990) 161–214), using 9-fluorenyl methoxycarbonyl (Fmoc) amino acids on a 9050 peptide synthesis unit from the MilliGen company. In the case of amino acids with different optical isomers, only the L forms have been described in the following examples, though the use of the D isomers has either only an insignificant influence on the adhesion effectiveness of the peptides, or none at all. Cleavage of the protecting groups and release of the peptides was effected, according to the details provided by the manufacturer, either with trifluoroacetic acid (TFA)/thioanisole/ethandithiol/anisole (90%/5%/3%/2%) or with TFA/phenol (95%/5%). Purification was effected by a linear gradient of buffer A to buffer B (buffer A: 0.1% TFA, buffer B: 90% acetonitrile in buffer A) on a VYDAC $C_{18}$ HPLC column (dimensions 250×30mm) at a flow rate of 9 ml/min. After that, the peptides were lyophilised in a Hetosicc freeze drying unit from the NUNC company at <0–04 mbar.

The amino acid sequences were identified by analysing protein sequences on a gas phase sequencing automat, 477A model, from Applied Biosystems. The phenylthiohydantoin amino acids were analysed on the 120A PTH analyser from the same manufacturer, coupled on-line.

TABLE 1

Control peptides used in the context of the present invention
The amino acids are shown in the one-letter code)

| DESIGNATION | SEQUENCE | CELL ADHESION [%] | δ [%] |
|---|---|---|---|
| FN | | 100.0 | 0.05 |
| IVA1 (SEQ ID NO: 28) | V-T-G-R-G-D-S-P-A-(C) | 93.9 | 0.34 |
| IVA1b (SEQ ID NO: 29) | G-R-G-D-S-(C) | 93.8 | 1.60 |
| P-15 (SEQ ID NO: 30) | G-T-P-G-P-Q-G-I-A-G-Q-R-G-V-V-(C) | 62.1 | 1.50 |
| SVTLG (SEQ ID NO: 31) | S-V-T-L-G-(C) | 72.1 | 3.39 |
| BSA | | 4.1 | 0.83 |

TABLE 2

Determining the effect of selected adhesion peptides in promoting cell/cell adhesion (The amino acids are shown in the one-letter code) using the cell adhesion test with HDF cells

| DESIGNATION | SEQUENCE | CELL ADHESION [%] | δ [%] |
|---|---|---|---|
| AP#1 | Q-I-D-F-N-R-L-F-T-H-P-V-T-D-L-F-D-P-(C) | 72.5 | 4.2 |
| AP#2 | G-I-E-T-P-L-P-K-K-E-L-L-L-P-(C) | 44.1 | 11.0 |
| AP#3 | S-I-Q-R-D-N-Y-A-E-L-L-D-D-(C) | 47.8 | 2.2 |
| AP#4 | L-S-C-G-K-E-Y-V-E-L-L-D-G-(C) | 77.1 | 4.8 |
| AP#5 | G-V-V-S-T-P-L-V-N-L-I-N-G-(C) | 53.2 | 5.5 |
| AP#6 | G-I-V-R-T-P-L-A-E-L-L-D-G-(C) | 69.0 | 5.8 |
| AP#7 | G-I-V-R-T-P-_-A-E-L-L-D-G-(C) | 103.3 | 8.1 |
| AP#8 | G-I-V-R-T-P-L-A-E-L-_-_-_-(C) | 78.2 | 1.5 |
| AP#9 | G-I-V-R-T-P-L-_-_-_-_-_-_-(C) | 93.0 | 2.2 |
| AP#10 | G-G-G-S-G-G-G-S-S-G-S-G-(C) | 27.5 | 0.1 |
| AP#11 | G-G-G-A-G-G-G-S-S-G-S-G-(C) | 30.5 | 5.0 |
| AP#12 | T-V-L-R-N-I-Q-E-L-L-D-G-E-(C) | 74.2 | 2.6 |
| AP#13 | I-V-R-T-P-L-A-E-L-L-D-G-(C) | 37.3 | 3.6 |
| AP#14 | I-V-R-T-P-_-A-E-L-L-D-G-(C) | 27.0 | 2.2 |

TABLE 2-continued

Determining the effect of selected adhesion peptides in promoting cell/cell adhesion (The amino acids are shown in the one-letter code) using the cell adhesion test with HDF cells

| DESIGNATION | SEQUENCE | CELL ADHESION [%] | δ [%] |
|---|---|---|---|
| AP#15 | R-T-P-L-A-E-L-L-D-G-(C) | 28.5 | 2.2 |
| AP#16 | R-T-P-_-A-E-L-L-D-G-(C) | 21.4 | 3.0 |
| AP#17 | L-A-E-L-L-D-G-E-G-Q-T-A-D-(C) | 13.1 | 0.5 |
| AP#18 | L-A-E-L-L-D-G-E-G-Q-(C) | 11.9 | 0.3 |
| AP#19 | L-A-E-L-L-D-G-E-G-(C) | 51.9 | 2.8 |
| AP#20 | L-A-E-L-L-D-G-E-(C) | 54.1 | 0.9 |
| AP#21 | L-A-E-L-L-D-G-(C) | 43.5 | 4.6 |
| AP#22 | L-A-E-L-L-E-G-(C) | 18.8 | 0.6 |
| AP#23 | L-A-E-L-L-L-G-(C) | 26.4 | 1.8 |
| AP#24 | A-E-L-L-D-G-(C) | 32.7 | 4.3 |
| AP#25 | E-L-L-D-G-(C) | 47.7 | 2.3 |
| AP#26 | L-L-D-G-(C) | 31.3 | 3.5 |
| AP#27 | L-D-G-(C) | 23.3 | 2.7 |
| BSA | | 4.1 | 0.8 |

δ [%] = standard deviation in %

2. Coupling the Peptides to Bovine Serum Albumin (BSA) as the Carrier Protein

The peptides provided with a C-terminal cysteine were coupled via the reactive maleimide group of the BSA activated with the bifunctional reagent sulphosuccinimidyl-4-(N-maleimidomethyl)-cyclohexane-1-carboxylate (sulpho-SMCC). To do this, the peptides were first reduced with REDUCTACRYL™ (agent, cleaving interpeptide disulfide bridges) (PIERCE). in order to remove any interpeptide disulphide bridges present. Per μmol of peptide (simple surplus). 2.2 mg of activated BSA (Bovine Serum Albumin) (PIERCE) were used. The coupling time was 16 hours at 4° C. and 2 hours at room temperature (RT). Any non-coupled peptide was removed from the conjugate by means of a MIKROSEP™ (centrifuge tube containing a membrane having an exclusion volume of 10 kD) Microconcentrator (Filtron Technology Corp.) with an exclusion volume of 10 KD.

3. Binding the Test Substances to Polystyrene

50 μl each of the peptide/BSA conjugates or the peptides were placed, in different concentrations, in the wells of a 96-well flat-bottomed microtiter plate (DYNATECH). After drying for 2 hours at 37° C., unbound peptide/BSA conjugate or peptide is removed by washing with phosphate-buffered saline solution (PBS) several times. In order to prevent the non-specific adhesion of the cells to polystyrene, all the wells were subsequently saturated for 30 min. at 37° C. with heat-denatured BSA (2 mg/ml). Following that, it was once again washed with PBS.

As a positive control for the adhesion capacity, bovine fibronectin (Paesel & Lorey, 1 mg/ml) was used, and heat-denatured BSA (2 mg/ml) as a negative control; this is not capable of influencing intercellular adhesion.

4. Determining Biological Activity 4.1 Cell Adherence Test

The cell adherence test was performed with AKR-2B mouse fibroblasts (Shipley et al., Cancer Res. 44 (1984) 710–716) and human dermal fibroblasts (HDF, removed from the lower arm, 18th passage). AKR-2B cells were cultivated in McCoy's medium (10% calf serum), and HDF cells in Dulbecco's modified eagle medium (DMEM) in the presence of 10% foetal calf serum (FCS) and 1% streptomycin/penicillin. For the adherence test, the cells were washed twice with protein-free HYBRI-MAX™ (medium for culture of hybridoma cell types containing 1 mM $Mn^{2+}$ and 0.02% heat-denatured BSA) medium (SIGMA) and then taken up in Hybri-Max (1 mM $Mn^{2+}$, 0.02% heat-denatured BSA). In this way, it was largely ensured that neither protein components from the culture medium, nor serum components, such as fibronectin for example, could influence the adherence test. In each well of the microtiter plate previously filled with test substance (peptide concentration per well: approx. 35 nmol), 200 μl of the cell suspension taken up in HYBRI-MAX™ (medium for culture of hybridoma cell types containing 1 mM $Mn^{2+}$ and 0.02% heat-denatured BSA) (1 mM $Mn^{2+}$, 0.02% heat-denatured BSA) ($1.5 \times 10^5$ cells/well) were pipetted and incubated for 1 hour in an incubator at 37° C., 5% $CO_2$ atmosphere. After that, the supernatant was decanted off, and non-adhered cells were removed by washing with PBS. The adhered cells were fixed for 0.5 min with methanol and stained with the MERCK HEMACOLOR™ (colution for fast staining in microscopy) reagent kit in order to quantify the number of cells.

For some selected conjugates, dilution series were included in order to determine binding constants for AKR-2B cells. For this purpose, the peptide/BSA conjugates were diluted in PBS, and 50 μl each of these dilutions were placed in the wells of a microtiter plate. Incubation and all the other steps were performed according to the method described above. After the readings had been plotted graphically, the difference between the figure for the maximum cell adherence and the zero value could be formed, and the $EC_{50}$ values shown in Tab. 3 as a measure of the semi-maximum cell adherence could be read off from the line of the curve.

4.2 Competitive Inhibition Test

Via the specific saturation of surface receptors (shown schematically in FIG. 3E), it is possible, in the case of soluble peptides, to measure an inhibitory effect on the adhesion of test cells (AKR-2B). In the experiment described here, a selected peptide/BSA conjugate corresponding to a peptide concentration of 10 nmol/well was placed in the microtiter plates and incubated for 2 hours at 37° C. Unsaturated binding sites in the culture vessel were subsequently saturated for 30 minutes with heat-denatured BSA (2 mg/ml). The peptides were dissolved in HYBRI-MAX™ (medium for culture of hybridoma cell types containing 1 mM $Mn^{2+}$ and 0.02% heat-denatured BSA) Medium (0.02 % BSA, 1 mM $Mn^{2+}$), and the pH was adjusted to a level of 7.2 to 7.4. Following that, the peptide solutions were treated with Reductacryl®. In the case of peptides which do not contain any cysteine, this step can be dispensed with. From these stock solutions, dilution series were prepared in HYBRI-MAX™ (medium for culture of hybridoma cell types containing 1 mM $Mn^{2+}$ and 0.02% heat-denatured BSA) medium (1 mM $Mn^{2+}$, 0.02% heat-denatured BSA), and added to the AKR-2B cells taken up in the same medium. After that, the specimens were incubated for 10 minutes at 37° C., while being gently shaken. The cells pre-treated in this way ($1.5 \times 10^5/200$ μl) were subsequently transferred to the conjugate-coated microtiter plates. The further treatment of the test plates was performed by analogy with 4.1.

The inhibitory effect of the peptides is shown in Tab. 4 as the difference between the 100% figure (control, with no peptide in the medium), and the maximum measured reduction in cell adherence at a peptide concentration of 1 μmol/well. A figure of 100% would mean complete inhibition, i.e. the maximum effect.

4.3 Chemotaxis Test

In addition to wound contraction, the epithelialisation of the wound as a result of the migration of cells from the edges of wounds plays a significant role in wound repair. Some selected peptides were investigated in chemotaxis tests in order to study their ability to simulate the migration of HDF cells. The test was conducted in accordance with Scharffetter-Kochanek et al. (J. Invest. Dermatol. 98 (1992) 3–11) in modified Boyden chambers. In the lower cavity of the Boyden chamber, 210 μl DMEM (control) or the potential chemoattractant taken up in the same volume of DMEM were placed. As a positive control, collagen I (300,000 g/ml, 100 μg/ml) and human fibronectin (Boehringer, 25 μg/ml) were used. $2 \times 10^5$ cells were pipetted into the upper Boyden chamber (volume 810 μl). The incubation time was 4 hours at 37° C. The results for the peptides investigated are summed up in Tab. 5, with the figures for the medium control already having been deducted from these readings.

5. Results

Results of the Adherence Test:

As was to be expected, conjugates of BSA as the carrier molecule and control peptides containing the RGD sequence (IVA1 and IVA1b) possess adherence promoting effects for HDF cells which are similarly good to those of fibronectin (Tab. 1). Both the collagen fragment P-15 and the thrombosponding consensus sequence, SVTLG, are slightly less effective in the concentration range selected. BSA to which no peptide was coupled exhibited virtually no adherence promoting effect.

Tab. 2 sums up the figures obtained with HDF cells in the adherence test for the peptides of the invention. The sequences of the peptides AP#1 to AP#27 are shown as SEQ ID NO:1 to SEQ ID NO:27 in the sequence protocol. In order to be able to characterise in greater detail epitopes with a minimal adhesion effect and in order to delimit them further, some of the 13 amino acid long sequence motifs were taken as the starting point and then some peptide variants were prepared and tested, shortened step by step at the amino terminus by one or more amino acids, as were, in addition, some internal deletion variants and peptides with carboxy terminal extensions. From the results (cf. Tab. 2), it becomes apparent that the amino terminal deletion of the amino acid glycine leads to a distinct reduction in effectiveness (cf. AP#6 and AP#7 compared to AP#13 and AP#14). The reduction in effectiveness is not, however, due to the mere absence of one or more amino acids, since the surprising result was obtained that variant AP#7, which, compared to AP#6, is characterised by an internal deletion of the amino acid leucine in position 7, actually exhibits a significantly improved adherence effectiveness compared to AP#6. For the variants AP#8 and AP#9, which are truncated at the carboxy terminal end and which have the amino acid glycine at the amino terminus, good effectiveness was likewise surprisingly established, it being equal or even superior to the adherence promoting effect of the complete AP#6 sequence. Compared to AP#8, sequence AP#9, which is one amino acid shorter, exhibited greater effectiveness. Sequences AP#8 and AP#9 or fragments thereof are therefore suitable as starting points for the development of further adhesion peptides which effectively influence the adhesion capacity of eukaryotic cells between each other (e.g. by varying the length and/or sequence of amino acids, by adding or deleting individual amino acids).

The results obtained with the sequences AP#8 and AP#9 confirm that the amino terminal amino acid glycine is of particular significance for the efficacy of the adhesion peptide, as can already be seen from a comparison of the results for AP#6 and AP#13 or AP#7 and AP#14, respectively.

As can already be seen from the studies with the peptides AP#7, AP#14, AP#16 and AP#24, the amino acid leucine (Leu) in position 7 (Aa7) does not convey any adherence facilitating or promoting effect. On the basis of the present results, the sequence Gly-Ile-Val-Arg-Thr-Pro (SEQ ID NO: 32)

is therefore preferred for peptides with a length of at least 9 amino acids in the context of the present invention.

One main feature which the most preferred adhesion effective peptides have in common is the carboxy terminal end of the peptides, which is laid down by the definition in claims 1 to 3 (with n=m=0), preference being given to the use of the amino acid glycine as the terminal amino acid (i.e. Aa1=Gly). Other conceivable amino acids in this position of the sequence are proline (cf. AP#1, AP#2) and aspartic acid (cf. AP#3). As an exception to this definition, it has been found, in the context of the present invention, that it is possible to extend this defined amino acid sequence at the carboxy terminal end of the peptides by up to two optional other amino acids, preferably Glu and/or Gly, without substantially reducing the positive effect of the cell/cell interaction. If a suitable amino acid AaX or amino acid combination AaX-AaY is selected, it is even possible that there may be an increased adherence promoting effect (cf. AP#19 and AP#20 compared to AP#21).

Other variants with sequence extensions at the carboxy terminus are as a rule considerably less effective compared to comparable peptides with no extension or compared to variants with only one additional amino acid AaX. The peptide referred to as AP#17 possesses the same sequence length as the peptides AP#3 to AP#6, though the sequence pattern which it has in common with sequence AP#6 (namely Aa7 to Aa1) is shifted by 6 amino acids in the direction of the carboxy terminus. In a similar manner, there is only an overlap of seven amino acids between the peptides AP#18 and AP#15, despite their having the same sequence length. Compared to the reference peptide AP#21, which only possesses these seven carboxy terminal amino acids (Aa7 to Aa1) of the adhesion peptides AP#6 and AP#15 respectively, and compared to AP#17 and AP#18, which are extended by 6 and 3 amino acids respectively beyond the carboxy terminal glycine, AP#17 and AP#18 only have a basal adhesion promoting effect. This means that sequence extensions with a length of 3 amino acids or more beyond the carboxy terminal end referred to as Aa1 in accordance with the invention (where n=0) exert disturbing effects on the positive influence on cell/cell adherence. The influence of carboxy terminal sequence extensions with a length of fewer than 3 amino acids, i.e. beyond the amino acid defined as Aa1, is relatively minor, though the adhesion peptides extended by up to 3 amino acids tend to behave either in a neutral or in a slightly adhesion promoting manner compared to the peptides ending with Aa1 at the carboxy terminus, as far as the intercellular interactions are concerned.

The section with the greatest sequence homology between the peptides AP#3-AP#7 and AP#13-AP#25 is located in the carboxy terminal region, especially in the sequence Glu-Leu-Leu-Asp-Gly.

The substitution of aspartic acid in position 2 (Aa2) by glutamic acid (acid function is maintained), or by leucine (cf. AP#21 compared to AP#22 and AP#23 in Tab. 2) leads to a somewhat reduced adherence efficacy.

What is remarkable is that even with the tripeptide Leu-Asp-Gly (AP#27) a significant adhesion promoting effect is still detectable.

In summary, these studies show that various factors have a substantial influence on the effect of the peptide sequences of the invention on cell/cell interaction. An amino terminal glycine, for example, and the carboxy terminal core sequence Glu-Leu-Leu-Asp-Gly (ELLDG, corresponding to AP#25) play a major role in adhesion peptides with more than 5 and preferably with 12 to 14 amino acids, and internal sequence variations in the remaining positions (such as the internal deletion variant AP#7, for example) can surprisingly even possess improved adhesion promoting properties compared to AP#6. In contrast to this, sequence extensions at the carboxy terminus mainly have an inhibitory influence.

Other peptides obtained by exchanging amino acids were likewise investigated in the context of the present invention to establish their capacity to modify the adhesion capacity of eukaryotic cells. The results are shown in Tab. 2. The sequence pattern AP#10, like the almost identical adhesion peptide AP#11 (different from AP#10 in that the amino acid Aa9=Ser has been exchanged for Aa9=Ala), possesses a significant adhesion modifying effect. Particularly good effectiveness was measured with the sequence AP#1, an 18 amino acid long adhesion peptide containing the carboxy terminal amino acid sequence Asp-Leu-Phe-Asp-Pro (corresponding to Aa5-Aa4-Aa3-Aa2-Aa1).

In order to establish binding constants for the peptides of the invention, dose effectiveness curves on AKR-2B cells were recorded for some selected conjugates. The $EC_{50}$ values shown in Tab. 3 as a measure of semi-maximum cell adherence were read off from the curve concerned (plotted: cell adherence versus peptide concentration). Low $EC_{50}$ values mean that only small quantities of the substances need to be used in order to achieve a semi-maximum effect, in other words that the substance is very effective.

Compared to the control peptide IVA1 containing the amino acid sequence "RGD", all the other peptide/carrier conjugates tested exhibit an adhesion promoting effect which is lower by at least a factor of 30 (AP#6). Nevertheless, in this system, all the peptides of the invention are more effective, by about a factor of 2–3, than the thrombospondin control peptide "SVTLG". The lower effectiveness of the peptides of the invention compared to IVA1 is presumably a consequence of the different mechanisms by which they work. As already mentioned above at a different point, the "RGD" sequence is recognised by cell surface receptors of the integrin type, whereas the peptides of the invention are allocated to the field of cell/cell interaction by virtue of the way in which they work, meaning that a functional activity is developed by a different type of cell surface receptors. The readings obtained are thus directly dependent on the number of functional receptors on the test cells for the peptide epitope concerned. In vitro, AKR-2B cells presumably express far more receptors of the integrin type as cell adhesion molecules. All in all, very uniform values were measured for the peptides of the invention, while the lowest $EC_{50}$ values were obtained for the peptides AP#3, AP#6 and AP#7. Even with the pentapeptide "ELLDG", a better binding constant was obtained compared to the control, "SVTLG".

TABLE 3

| Designation | $EC_{50}$ [pmol/well] |
| --- | --- |
| IVA1 | 0.73 |
| SVTLG | 64.5 |
| AP#1 | 32.9 |
| AP#2 | 39.8 |
| AP#3 | 24.7 |
| AP#4 | 30.0 |
| AP#6 | 21.5 |
| AP#7 | 27.0 |
| AP#8 | 41.7 |
| AP#9 | 50.7 |
| AP#12 | 29.0 |
| AP#25 | 42.0 |

Results of the Adherence Inhibition Test:

For the peptides of the invention available in soluble form, i.e. in a form not bound to carrier molecules, it is possible to detect adhesion inhibiting properties which come about as a result of the specific blockade of epitopes on surface receptors of the test cells (cf. FIG. 3E). In order to demonstrate these effects, selected peptides were tested with regard to their capability to effect a competitive inhibition of the adherence of the test cells to prepared conjugate of BSA and the AP#2 peptide.

The AP#2 peptide was selected as an internal standard. Compared to most of the other peptides of the invention (cf. Tab. 2), the adhesion promoting properties of BSA/AP#2 conjugates lie within a region of semi-maximum effectiveness. Experience has shown that, in order to detect inhibitory effects, it is favourable to measure in a range of less than optimum effect, since otherwise weak inhibitory effects might not be detected.

The IVA1 peptide containing the sequence Arg-Gly-Asp ("RGD") was used as a negative control. This peptide develops its effect via receptors of the integrin type (cf. FIGS. 1–3), i.e. this mechanism is the specific interaction of cells with components of the ECM (cell/matrix interaction). In the case under study here, which is concerned with the interaction between cell adhesion molecules in the context of a competitive test, it was assumed that the IVA1 peptide does not exhibit any specific effect, because the interaction takes place in a different mechanical way (see above) compared to the cell/cell interaction. Tab. 4 sums up the results of this investigation using the adhesion peptides AP#3, AP#4, AP#6, AP#7, AP#17 and AP#25 in accordance with the invention. As was to be expected, the AP#2 peptide (competition with itself) exhibits a highly significant inhibitory effect on the attachment of AKR-2B cells. Similarly powerful effects are also measured for the peptides AP#6 and AP#7, however, and also, though with slightly less efficiency, for the peptides AP#3, AP#4 and the short peptide AP#25. This is an unambiguous indication that the adhesion mediating function of these peptide sequences can be traced to the interaction with a common epitope on a cellular receptor. As was to be expected, the peptide AP#17, which is an example of peptides extended beyond Aa1 at the carboxy terminal end, and IVA1, which possesses the RGD sequence (Arg-Gly-Asp) which is effective in cell/matrix interactions, exhibited virtually no effect in this system.

TABLE 4

Investigation of the Inhibitory Effect of Selected Adhesion Peptides

| Peptide (concentration 1 μmol/well) | Inhibition [Z] |
| --- | --- |
| AP#2 (internal standard) | 51.5 |
| AP#3 | 17 |
| AP#4 | 19.9 |
| AF#6 | 53 |
| AP#7 | 49.2 |
| AP#17 | 5.4 |
| AP#25 | 18.1 |
| IVA1 (negative control) | 2.6 |

Results of the Chemotaxis Test:

The results of the chemotaxis test are shown in Tab. 5, taking the peptides AP#3 and AP#7 as examples. Apart from their importance in cell/matrix interactions, the chemotactic effect of a number of ECM components is known. Collagen and fibronectin in particular are effective activators of cell migration (Guo et al., J. Cell Sci. 96 (1990) 197–205).

After deducting the readings for the medium control, both the peptides tested exhibit a distinct chemotactic effect for HDF cells when compared to collagen and fibronectin (positive controls) in the dosage used. As a result of this study, it has been possible to demonstrate that the adhesion peptides of the present invention can promote the migration of human cells in vitro and thus possess a clear potential for the active acceleration of wound repair processes.

TABLE 5

Chemotaxis Test Using HDF Cells

| | Concentration | Avge. no. of cells per field of vision | Chemotactic migration [%] | δ [%] |
| --- | --- | --- | --- | --- |
| Collagen | 0.3 nmol/ml | 45.7 | 100.0 | 16.3 |
| Fibronectin | 0.6 nmol/ml | 43.9 | 96.0 | 5.6 |
| AP#3 | 1 μmol/ml | 11.1 | 24.3 | 0.2 |
| AP#7 | 1 μmol/ml | 10.9 | 23.9 | 14.2 |

Description of the drawings

Schematic diagram of cell/cell and cell/matrix interactions FIG. 1) Contacts between the cell and the ECM components mediated mainly by surface receptors of the integrin type, shown here taking the epitope Arg-Gly-Asp ("RGD") as an example (A). Intercellular adhesion contacts by cell adhesion molecules (CAMs) are shown in (B), and inducible luminal CAMs in (C).

FIG. 2) Highly specific peptides derived from cell adhesion molecules which are present coupled to suitable carrier molecules are capable of supporting CAM-specific cellular interactions (D). In a suitable galenical preparation, it is possible, with these conjugates, to promote cell attachment processes, such as the rate at which skin grafts grow on.

FIG. 3) This illustration depicts the manner in which free peptides, i.e. those not conjugated to carrier molecules, can inhibit cellular adhesion processes by means of the specific saturation of binding sites on the CAMs (E).

Abbreviations

AP# adherence/adhesion peptide

Aa amino acid

BSA bovine serum albumin

δ standard deviation

CAM cell adhesion molecule

DMEM Dulbecco's modified eagle medium $EC_{50}$ effective concentration (measure of the semi-maximum effectiveness)

ECM extracellular matrix

FCS foetal calf serum

HDF human dermal fibroblasts

KD kilodalton

KLH keyhole limpet haemocyanin

PBS phosphate-buffered saline solution

PEG polyethylene glycol

RGD arginine-glycine-aspartic acid

RT room temperature

TFA trifluoroacetic acid

We claim:

1. Method for modifying the adhesion capacity of eukaryotic cells between each other, comprising contacting said eukaryotic cells with a composition comprising a peptide having amino acid sequence Aa3-Aa2-Aa1,
wherein
Aa1 is Gly, Pro or Asp,
Aa2 is Asp, Leu, Asn or Ser, and
Aa3 is Leu, Ile, Phe or Gly,
and wherein Aa1 forms the terminal amino acid at the carboxy terminal end of the peptide, wherein the amino acid sequence at the carboxy terminal end of the peptide is optionally extended by up to 2 other amino acids, and wherein the amino acid sequence could be extended at the amino terminus (Aa3) up to a length of 30 amino acids.

2. The method according to claim 1 wherein said peptide has the amino acid sequence Aa3-Aa2-Aa1-(AaX)$_n$-(AaY)$_m$ (SEQ ID NO: 33),
wherein
n is either 0 or 1,
m is either 0 or 1 when n=1, and
Aa1 indicates the terminal amino acid at the carboxy terminal end of the peptide when n=m=0, and wherein
AaX and AaY are any optional amino acid in each case,
Aa1 is Gly, Pro or Asp,
Aa2 is Asp, Leu, Asn or Ser, and
Aa3 is Leu, Ile, Phe or Gly.

3. The method according to claim 1 wherein said peptide has a length of 3 to 30 amino acids.

4. The method according to claim 2 wherein said peptide has at least the amino acid sequence Aa4-Aa3-Aa2-Aa1-(AaX)$_n$-(AaY)$_m$ (SEQ ID NO: 34),
where
Aa4 is Leu or Ser.

5. The method according to claim 4 wherein the peptide has at least the amino acid sequence Aa5-Aa4-Aa3-Aa2-Aa1-(AaX)$_n$-(AaY)$_m$ (SEQ ID NO: 35),
where
Aa5 is Glu, Ser, Asp or Asn.

6. The method according to claim 1 wherein the peptide has a length of 6 to 30 amino acids, the amino acid at the amino terminal end of the peptide being Gly, Ser, Leu, Ile, Arg or Thr.

7. The method according to claim 6 wherein the peptide has a length of 12 to 14 amino acids.

8. The method according to claim 7 wherein the amino acid at the amino terminal end of the peptide is Gly.

9. The method according to claim 1 wherein Aa3 is Leu.

10. The method according to claim 5 wherein Aa5 is Glu.

11. The method according to claim 1 wherein said peptide has the amino acid sequence Leu-Asp-Gly (SEQ ID NO: 27).

12. The method according to claim 1 wherein said peptide has an amino acid sequence selected from the group consisting of SEQ ID NO: 25, 21, 7, 6, 12, 10, 11, 1, 19 and 18.

13. A peptide comprising the amino acid sequence Glu-Leu-Leu-Asp-Gly (SEQ ID NO: 25) or Leu-Ala-Glu-Leu-Leu-Asp-Gly (SEQ ID NO: 21).

14. The method of claim 1 wherein said peptide is bound to a carrier.

15. The method of claim 14 wherein said carrier is bovine serum albumin, keyhole limpet haemocyanin, collagen, polylysin, an immunoglobulin or a polysaccharide.

16. The method according to claim 15 wherein said polysaccharide is hyaluronic acid.

17. The method according to claim 14 wherein said peptide is bound at its carboxy terminal end to the carrier via a cysteine residue.

18. The method of claim 14 wherein at least two peptides are bound to said carrier.

19. The method according to claim 1 wherein said eukaryotic cells are endothelial cells.

20. The method according to claim 1 wherein said eukaryotic cells are endothelial cells lining vessels in artificial blood vessels.

21. The method according to claim 1 wherein said eukaryotic cells are human dermal or epidermal cells.

22. The method of claim 1 wherein said modifying comprises reducing the adhesion between said eukaryotic cells in vitro.

23. The method according to claim 1 wherein said modifying comprises attracting said eukaryotic cells such that said peptide is a chemotactic attractor.

24. The method of claim 1 further comprising determining the adhesion capacity of said eukaryotic cells.

25. The method of claim 1 wherein said composition comprises one or more of said peptide and, optionally contains at least one carrier adjuvant or additive.

26. The method according to claim 1 wherein a single peptide is bound to a single carrier unit.

* * * * *

SEQUENCE LISTING (1) GENERAL INFORMATION:

(iii) NUMBER OF SEQUENCES: 35

(2) INFORMATION FOR SEQ ID NO: 1:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..18
        (D) OTHER INFORMATION:/note= "AP#1"

(xi) SEQUENCE DESCRIPTION: SEQ ID NO: 1:

Gln Ile Asp Phe Asn Arg Leu Phe Thr His Pro Val Thr Asp Leu Phe
1               5                  10                 15

Asp Pro (2) INFORMATION FOR SEQ ID NO: 2:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..14
        (D) OTHER INFORMATION:/note= "AP#2"

(xi) SEQUENCE DESCRIPTION: SEQ ID NO: 2:

Gly Ile Glu Thr Pro Leu Pro Lys Lys Glu Leu Leu Leu Pro
1               5                  10

(2) INFORMATION FOR SEQ ID NO: 3:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..13
        (D) OTHER INFORMATION:/note= "AP#3"

(xi) SEQUENCE DESCRIPTION: SEQ ID NO: 3:

Ser Ile Gln Arg Asp Asn Tyr Ala Glu Leu Leu Asp Asp
1               5                  10

(2) INFORMATION FOR SEQ ID NO: 4:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:

(A) NAME/KEY: peptides
            (B) LOCATION:1..13
            (D) OTHER INFORMATION:/note= "AP#4"

(xi) SEQUENCE DESCRIPTION: SEQ ID NO: 4:

Leu Ser Cys Gly Lys Glu Tyr Val Glu Leu Leu Asp Gly
1               5                   10

(2) INFORMATION FOR SEQ ID NO: 5:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..13
            (D) OTHER INFORMATION:/note= "AP#5"

(xi) SEQUENCE DESCRIPTION: SEQ ID NO: 5:

Gly Val Val Ser Thr Pro Leu Val Asn Leu Ile Asn Gly
1               5                   10

(2) INFORMATION FOR SEQ ID NO: 6:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..13
            (D) OTHER INFORMATION:/note= "AP#6"

(xi) SEQUENCE DESCRIPTION: SEQ ID NO: 6:

Gly Ile Val Arg Thr Pro Leu Ala Glu Leu Leu Asp Gly
1               5                   10

(2) INFORMATION FOR SEQ ID NO: 7:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..12
            (D) OTHER INFORMATION:/note= "AP#7"

(xi) SEQUENCE DESCRIPTION: SEQ ID NO: 7:

Gly Ile Val Arg Thr Pro Ala Glu Leu Leu Asp Gly
1               5                   10

(2) INFORMATION FOR SEQ ID NO: 8:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:

(A) NAME/KEY: peptides
            (B) LOCATION:1..10
            (D) OTHER INFORMATION:/note= "AP#8"

(xi) SEQUENCE DESCRIPTION: SEQ ID NO: 8:

Gly Ile Val Arg Thr Pro Leu Ala Glu Leu
1               5                   10

(2) INFORMATION FOR SEQ ID NO: 9:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..7
            (D) OTHER INFORMATION:/note= "AP#9"

(xi) SEQUENCE DESCRIPTION: SEQ ID NO: 9:

Gly Ile Val Arg Thr Pro Leu
1               5

(2) INFORMATION FOR SEQ ID NO: 10:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..12
            (D) OTHER INFORMATION:/note= "AP#10"

(xi) SEQUENCE DESCRIPTION: SEQ ID NO: 10:

Gly Gly Gly Ser Gly Gly Gly Ser Ser Gly Ser Gly
1               5                   10

(2) INFORMATION FOR SEQ ID NO: 11:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..12
            (D) OTHER INFORMATION:/note= "AP#11"

(xi) SEQUENCE DESCRIPTION: SEQ ID NO: 11:

Gly Gly Gly Ala Gly Gly Gly Ser Ser Gly Ser Gly
1               5                   10

(2) INFORMATION FOR SEQ ID NO: 12:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:

(A) NAME/KEY: peptides
        (B) LOCATION:1..13
        (D) OTHER INFORMATION:/note= "AP#12"

(xi) SEQUENCE DESCRIPTION: SEQ ID NO: 12:

Thr Val Leu Arg Asn Ile Gln Glu Leu Leu Asp Gly Glu
1               5                   10

(2) INFORMATION FOR SEQ ID NO: 13:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..12
        (D) OTHER INFORMATION:/note= "AP#13"

(xi) SEQUENCE DESCRIPTION: SEQ ID NO: 13:

Ile Val Arg Thr Pro Leu Ala Glu Leu Leu Asp Gly
1               5                   10

(2) INFORMATION FOR SEQ ID NO: 14:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..11
        (D) OTHER INFORMATION:/note= "AP#14"

(xi) SEQUENCE DESCRIPTION: SEQ ID NO: 14:

Ile Val Arg Thr Pro Ala Glu Leu Leu Asp Gly
1               5                   10

(2) INFORMATION FOR SEQ ID NO: 15:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..10
        (D) OTHER INFORMATION:/note= "AP#15"

(xi) SEQUENCE DESCRIPTION: SEQ ID NO: 15:

Arg Thr Pro Leu Ala Glu Leu Leu Asp Gly
1               5                   10

(2) INFORMATION FOR SEQ ID NO: 16:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (ix) FEATURE:

```
            (A) NAME/KEY: peptides
            (B) LOCATION:1..9
            (D) OTHER INFORMATION:/note= "AP#16"

(xi) SEQUENCE DESCRIPTION: SEQ ID NO: 16:

Arg Thr Pro Ala Glu Leu Leu Asp Gly
1               5

(2) INFORMATION FOR SEQ ID NO: 17:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..13
            (D) OTHER INFORMATION:/note= "AP#17"

(xi) SEQUENCE DESCRIPTION: SEQ ID NO: 17:

Leu Ala Glu Leu Leu Asp Gly Glu Gly Gln Thr Ala Asp
1               5                   10

(2) INFORMATION FOR SEQ ID NO: 18:

(i) SEQUENCE CHARACTERISTICS:
            (A) LENGTH: 10 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..10
            (D) OTHER INFORMATION:/note= "AP#18"

(xi) SEQUENCE DESCRIPTION: SEQ ID NO: 18:

Leu Ala Glu Leu Leu Asp Gly Glu Gly Gln
1               5                   10

(2) INFORMATION FOR SEQ ID NO: 19:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..9
            (D) OTHER INFORMATION:/note= "AP#19"

(xi) SEQUENCE DESCRIPTION: SEQ ID NO: 19:

Leu Ala Glu Leu Leu Asp Gly Glu Gly
1               5

(2) INFORMATION FOR SEQ ID NO: 20:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (ix) FEATURE:
```

```
            (A) NAME/KEY: peptides
            (B) LOCATION:1..8
            (D) OTHER INFORMATION:/note= "AP#20"

(xi) SEQUENCE DESCRIPTION: SEQ ID NO: 20:

Leu Ala Glu Leu Leu Asp Gly Glu
1               5

(2) INFORMATION FOR SEQ ID NO: 21:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..7
            (D) OTHER INFORMATION:/note= "AP#21"

(xi) SEQUENCE DESCRIPTION: SEQ ID NO: 21:

Leu Ala Glu Leu Leu Asp Gly
1               5

(2) INFORMATION FOR SEQ ID NO: 22:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..7
            (D) OTHER INFORMATION:/note= "AP#22"

(xi) SEQUENCE DESCRIPTION: SEQ ID NO: 22:

Leu Ala Glu Leu Leu Glu Gly
1               5

(2) INFORMATION FOR SEQ ID NO: 23:

(i) SEQUENCE CHARACTERISTICS:
            (A) LENGTH: 7 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..7
            (D) OTHER INFORMATION:/note= "AP#23"

(xi) SEQUENCE DESCRIPTION: SEQ ID NO: 23:

Leu Ala Glu Leu Leu Leu Gly
1               5

(2) INFORMATION FOR SEQ ID NO: 24:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (ix) FEATURE:
```

(A) NAME/KEY: peptides
            (B) LOCATION:1..6
            (D) OTHER INFORMATION:/note= "AP#24"

(xi) SEQUENCE DESCRIPTION: SEQ ID NO: 24:

Ala Glu Leu Leu Asp Gly
1               5

(2) INFORMATION FOR SEQ ID NO: 25:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..5
            (D) OTHER INFORMATION:/note= "AP#25"

(xi) SEQUENCE DESCRIPTION: SEQ ID NO: 25:

Glu Leu Leu Asp Gly
1               5

(2) INFORMATION FOR SEQ ID NO: 26:

(i) SEQUENCE CHARACTERISTICS:
            (A) LENGTH: 4 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..4
            (D) OTHER INFORMATION:/note= "AP#26"

(xi) SEQUENCE DESCRIPTION: SEQ ID NO: 26:

Leu Leu Asp Gly
1

(2) INFORMATION FOR SEQ ID NO: 27:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..3
            (D) OTHER INFORMATION:/note= "AP#27"

(xi) SEQUENCE DESCRIPTION: SEQ ID NO: 27:

Leu Asp Gly
1

(2) INFORMATION FOR SEQ ID NO: 28:

(i) SEQUENCE CHARACTERISTICS:
            (A) LENGTH: 9 amino acids
            (B) TYPE: amino acid
            (D) TOPOLOGY: linear (ii) MOLECULE TYPE: peptide (ix) FEATURE:

```
            (A) NAME/KEY: peptides
            (B) LOCATION:1..9
            (D) OTHER INFORMATION:/note= "IVA1"

(xi) SEQUENCE DESCRIPTION: SEQ ID NO: 28:

Val Thr Gly Arg Gly Asp Ser Pro Ala
1               5

(2) INFORMATION FOR SEQ ID NO: 29:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..5
            (D) OTHER INFORMATION:/note= "IVA1b"

(xi) SEQUENCE DESCRIPTION: SEQ ID NO: 29:

Gly Arg Gly Asp Ser
1               5

(2) INFORMATION FOR SEQ ID NO: 30:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..15
            (D) OTHER INFORMATION:/note= "P-15"

(xi) SEQUENCE DESCRIPTION: SEQ ID NO: 30:

Gly Thr Pro Gly Pro Gln Gly Ile Ala Gly Gln Arg Gly Val Val
1               5                  10                  15

(2) INFORMATION FOR SEQ ID NO: 31:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (ix) FEATURE:
            (A) NAME/KEY: peptides
            (B) LOCATION:1..5
            (D) OTHER INFORMATION:/note= "SVTLG"

(xi) SEQUENCE DESCRIPTION: SEQ ID NO: 31:

Ser Val Thr Leu Gly
1               5

(2) INFORMATION FOR SEQ ID NO: 32:

(i) SEQUENCE CHARACTERISTICS:
            (A) LENGTH: 6 amino acids
            (B) TYPE: amino acid
            (D) TOPOLOGY: linear (ii) MOLECULE TYPE: peptide (ix) FEATURE:
```

```
            (A) NAME/KEY: peptides
            (B) LOCATION:1..6
            (D) OTHER INFORMATION:/note= "NH2-Terminus"

(xi) SEQUENCE DESCRIPTION: SEQ ID NO: 32:

Gly Ile Val Arg Thr Pro
1               5

(2) INFORMATION FOR SEQ ID NO: 33:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..5
        (D) OTHER INFORMATION:/note= "The amino acids can have the
            following meaning: Pos. 1 (=Aa3): Leu, Ile, Phe
            or Gly / Pos. 2 (=Aa2): Asp, Leu, Asn or Ser /
            Pos. 3 (=Aa1): Gly, Pro or Asp / Pos. 4 and 5
            (AaX, AaY): optional"

(xi) SEQUENCE DESCRIPTION: SEQ ID NO: 33:

Xaa Xaa Xaa Xaa Xaa
1               5

(2) INFORMATION FOR SEQ ID NO: 34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..6
        (D) OTHER INFORMATION:/note= "The amino acids can have the
            following meaning: Pos. 1 (=Aa4): Leu or Ser /
            meaning of the other amino acids as in SEQ.ID
            No. 33"

(xi) SEQUENCE DESCRIPTION: SEQ ID NO: 34:

Xaa Xaa Xaa Xaa Xaa Xaa
1               5

(2) INFORMATION FOR SEQ ID NO: 35:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: peptides
        (B) LOCATION:1..7
        (D) OTHER INFORMATION:/note= "The amino acids can have the
            following meaning: Pos. 1 (=Aa5): Glu, Ser, Asp
            or Asn / meaning of the other amino acids as in
            SEQ.ID No. 33 and SEQ.ID No. 34"

(xi) SEQUENCE DESCRIPTION: SEQ ID NO: 35:

Xaa Xaa Xaa Xaa Xaa Xaa Xaa
1               5
```